(12) United States Patent
McCarthy (10) Patent No.: US 7,951,196 B2
(45) Date of Patent: May 31, 2011

(54) ANNULOPLASTY RING FOR MITRAL VALVE PROLAPSE

(75) Inventor: Patrick M. McCarthy, Chicago, IL (US)

(73) Assignee: Edwards Lifesciences Corporation, Irvine, CA (US)

(*) Notice: Subject to any disclaimer, the term of this patent is extended or adjusted under 35 U.S.C. 154(b) by 655 days.

(21) Appl. No.: 11/345,936

(22) Filed: Feb. 2, 2006

(65) Prior Publication Data

US 2006/0129236 A1   Jun. 15, 2006

Related U.S. Application Data

(63) Continuation-in-part of application No. 10/834,556, filed on Apr. 29, 2004, now Pat. No. 7,294,148.

(51) Int. Cl.
*A61F 2/06* (2006.01)
(52) U.S. Cl. ..................... 623/2.36; 623/2.37
(58) Field of Classification Search ............... 623/2.36
See application file for complete search history.

(56) References Cited

U.S. PATENT DOCUMENTS

| | | | |
|---|---|---|---|
| 3,656,185 A | 4/1972 | Carpentier |
| 4,164,046 A | 8/1979 | Cooley |
| 4,217,665 A | 8/1980 | Bex et al. |
| 5,061,277 A | 10/1991 | Carpentier et al. |
| 5,104,407 A | 4/1992 | Lam et al. |
| 5,496,336 A | 3/1996 | Cosgrove et al. |
| 5,607,471 A | 3/1997 | Seguin et al. |
| 5,776,189 A | 7/1998 | Khalid |
| 6,102,945 A | 8/2000 | Campbell |
| 6,159,240 A | 12/2000 | Sparer et al. |
| 6,183,512 B1 | 2/2001 | Howanec, Jr. et al. |
| 6,250,308 B1 | 6/2001 | Cox |
| 6,258,122 B1 | 7/2001 | Tweden et al. |
| 6,419,696 B1 | 7/2002 | Ortiz et al. |
| 2002/0129820 A1 | 9/2002 | Ryan et al. |
| 2002/0169504 A1 | 11/2002 | Alferness et al. |

(Continued)

FOREIGN PATENT DOCUMENTS

EP     0338994     10/1989
(Continued)

OTHER PUBLICATIONS

Melo et al., Atrioventricular Valve Repair Using Externally Adjustable Flexible Rings, The Journal of Thoracic Cardiovascular Surgery, vol. 110, No. 5, 1995.

(Continued)

*Primary Examiner* — Corrine M McDermott
*Assistant Examiner* — Christopher D Prone
(74) *Attorney, Agent, or Firm* — AnneMarie Kaiser; Guy Cumberbatch (57) ABSTRACT

A mitral annuloplasty ring that has an outward and an upward posterior bow. The ring defines a closed, modified oval shape with a minor-major axis dimension ratio of between about 3.3:4 to 4:4. The ring is made of a material that will substantially resist distortion when subjected to the stress imparted thereon after implantation in the mitral valve annulus of an operating human heart. The outward and upward posterior bow of the annuloplasty ring corrects for pathologies associated with mitral valve prolapse, as seen with Barlow's syndrome for instance, in which the leaflets tend to be elongated or floppy. Desirably, the outward bow includes a more pronounced outward bulge having an angular extent that approximately equals the angular extent of the upward bow. Sections adjacent the outward bulge may be relatively straight.

20 Claims, 7 Drawing Sheets

U.S. PATENT DOCUMENTS

| | | |
|---|---|---|
| 2003/0033009 A1 | 2/2003 | Gabbay |
| 2003/0083742 A1 | 5/2003 | Spence et al. |
| 2003/0093148 A1* | 5/2003 | Bolling et al. ............... 623/2.36 |
| 2004/0006384 A1 | 1/2004 | McCarthy |

FOREIGN PATENT DOCUMENTS

| | | |
|---|---|---|
| EP | 1034753 | 9/2000 |
| WO | WO01/26586 | 4/2001 |
| WO | WO03041617 | 5/2003 |
| WO | WO2005034813 | 4/2005 |
| WO | WO2005/110290 | 11/2005 |
| WO | WO2007050506 | 5/2007 |

OTHER PUBLICATIONS

Alonso-Lei, M.D., et al., "Adjustable Annuloplasty for Triscupid Insufficiency,"The Annals of Thoracic Surgery, vol. 46, No. 3, pp. 368-369, Sep. 1988.

Carpentier-Edwards Classic Annuloplasty Ring with Duraflo Treatment Models 4425 and 4525 for Mitral and Tricuspid Valvuloplasty, Baxter Health Care Corporation, 1998.

* cited by examiner

ANNULOPLASTY RING FOR MITRAL VALVE PROLAPSE

RELATED APPLICATIONS

The present application is a continuation-in-part of prior application Ser. No. 10/834,556, filed Apr. 29, 2004, now U.S. Pat. No. 7,294,148, the disclosure of which is expressly incorporated by reference herein.

FIELD OF THE INVENTION

The present invention refers to a prosthetic annuloplasty ring for a mitral valve, in particular for correcting pathologies associated with mitral valve prolapse, for example, Barlow's syndrome or myxomatous disease.

BACKGROUND OF THE INVENTION

In the operation of the heart, returning blood enters the right atrium and passes through the tricuspid valve into the right ventricle. From there, blood is pumped through the pulmonary valve and the pulmonary artery to the lungs. Oxygenated blood enters the left atrium and passes into the left ventricle through the mitral valve. Healthy mitral valve leaflets "coapt" or meet near the middle of the blood flow path and are attached to papillary muscles within the interior of the left ventricle by a number of stringy chordae tendinae. During systole, the mitral valve closes and the aortic valve opens, thus preventing blood from regurgitating into the left atrium and forcing blood into the aorta, and from there throughout the body. Because of the high pressures associated with the left ventricle during systole, proper mitral valve function to prevent back flow through the system is extremely important.

Mitral regurgitation is one of the most common valvular malfunctions in the adult population. Mitral valve prolapse is the most common cause of mitral regurgitation in North America and is believed to affect at least 5 to 10 percent of the population in the U.S. Women are affected about twice as often as men. Mitral valve prolapse has been diagnosed as Barlow's syndrome, billowing or balloon mitral valve, floppy mitral valve, floppy-valve syndrome, myxomatous mitral valve, prolapsing mitral leaflet syndrome, or systolic click-murmur syndrome. Some forms of mitral valve prolapse seem to be hereditary, though the condition has been associated with Marfan's syndrome, Grave's disease, and other disorders.

Barlow's disease is characterized by myxoid degeneration and appears early in life, often before the age of fifty. Patients typically present with a long history of systolic murmur and may experience valve infection, arrhythmias and atypical chest pain. Some cases are asymptomatic, but a pronounced midsystolic click with or without late systolic murmur, usually indicates the presence of this disorder. South African cardiologist John B. Barlow was the first to interpret this auscultation syndrome, known for decades as an expression of a mitral valve prolapse. In Barlow's disease, one or both leaflets of the mitral valve protrude into the left atrium during the systolic phase of ventricular contraction. The valve leaflets are thick with considerable excess tissue, producing an undulating pattern at the free edges of the leaflets. The chordae are thickened, elongated and may be ruptured. Papillary muscles are also occasionally elongated. The annulus is dilated and sometimes calcified. Of course, some of these symptoms present in other pathologies, and therefore the present application will refer to mitral valve prolapse as a catch-all for the various diagnoses, including Barlow's syndrome.

Figure 1:
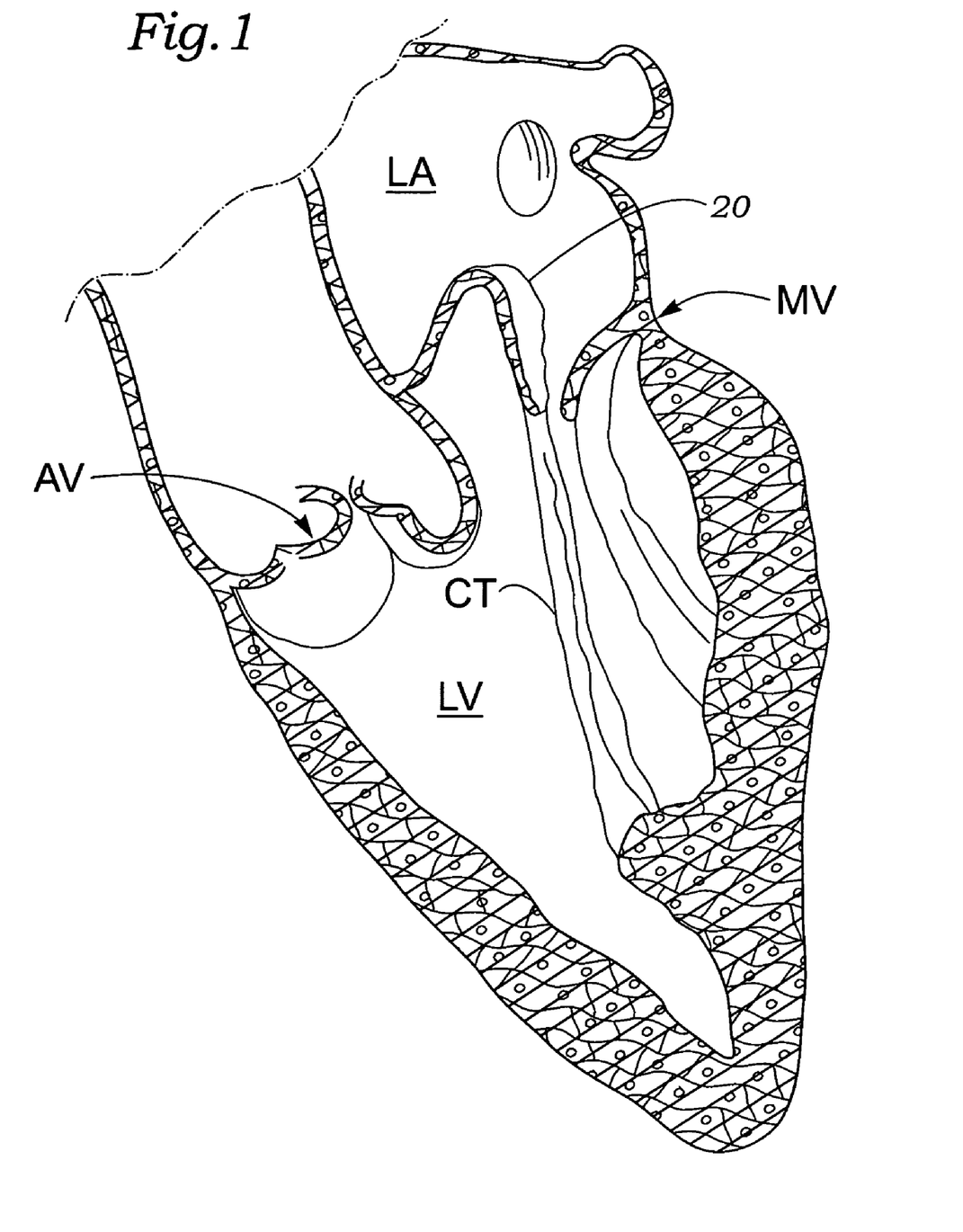
FIG. 1 is an enlarged sectional view of the left ventricle of a human heart illustrating one configuration of distended mitral valve leaflets seen with mitral valve prolapse.

FIG. 1 is an enlarged view of the left ventricle LV illustrating mitral valve prolapse, such as seen with Barlow's syndrome. One of the leaflets 20 of the mitral valve MV is shown thickened and lengthened from its normal configuration. As a result, the leaflet 20 is shown flopping upward into the left atrium LA. This excess tissue, or redundancy, often prevents the anterior and posterior leaflets from properly coapting, resulting in mitral regurgitation.

In patients with degenerative mitral valve disease, valve repairs using mitral valvuloplasty valve reconstruction, or annuloplasty have been the standards for surgical correction of mitral regurgitation and have provided excellent long-term results. A rigid support ring (e.g., Carpentier-Edwards Classic®), a semi-flexible ring (e.g., Carpentier-Edwards Physio®), or a flexible ring (e.g., Cosgrove-Edwards®) may be used. Other repair techniques include: quadrangular resection of the prolapsing portion of the posterior leaflet; transposition of the posterior leaflet to the anterior leaflet to correct anterior-leaflet prolapse; commissurotomy combined with ring annuloplasty; replacement of a chordae tendinae with sutures; and plication (or resection) of the anterior leaflet. A commonly used repair is the so-called "sliding technique" introduced by Dr. Alain Carpentier, which involves quadrangular resection followed by cutting the posterior leaflet and reconstruction to shorten this leaflet.

The advantages of repair over replacement have been widely demonstrated; however, studies have shown that mitral valve repair is performed in less than half of surgical procedures involving the mitral valve, and even fewer repairs are performed in patients with complex mitral regurgitation (e.g., Barlow's disease, bileaflet prolapse and annular calcification). Despite adequate tissue resection and placement of an annuloplasty ring or band, patients may have residual mitral regurgitation associated with systolic anterior motion (SAM) of the anterior leaflet. SAM occurs when the elongated leaflet is pulled into the left ventricular outflow tract (LVOT). This leads to partial LVOT obstruction and hemodynamic instability. This scenario is not an uncommon incident following an otherwise successful mitral valve repair and can be very difficult to treat with existing repair techniques and devices, and may require mitral valve replacement rather than the preferred of valve repair.

Figure 2A:
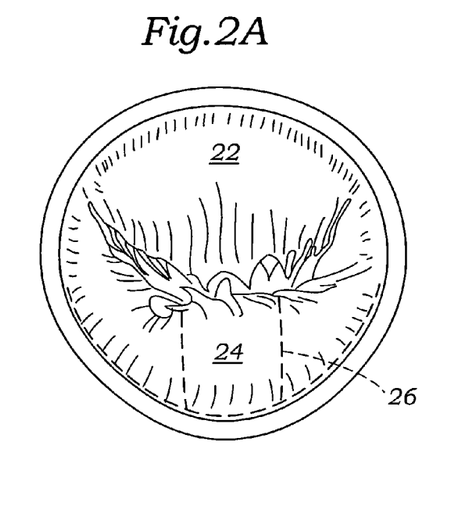
FIGS. 2A-2F are a series of plan views of a prior art surgical procedure for correcting a mitral valve that exhibits symptoms of mitral valve prolapse.
Figure 2B:
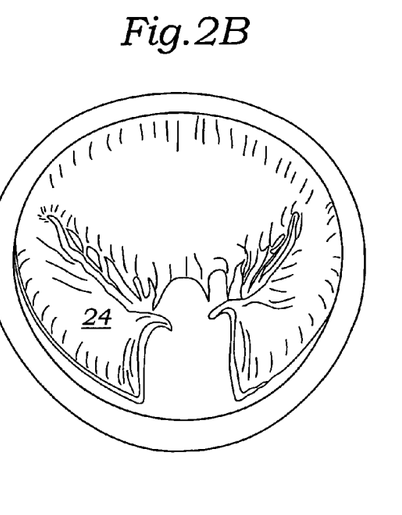
Figure 2C:
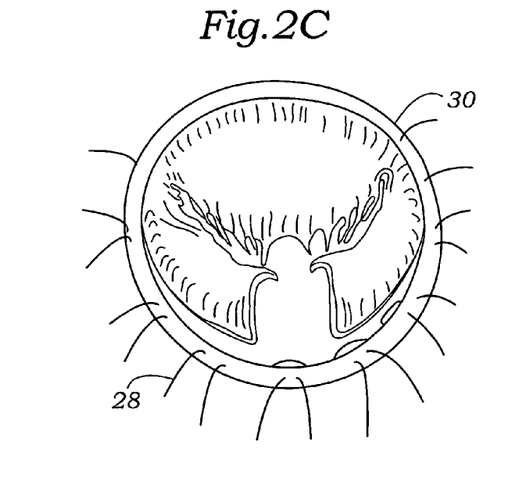
Figure 2D:
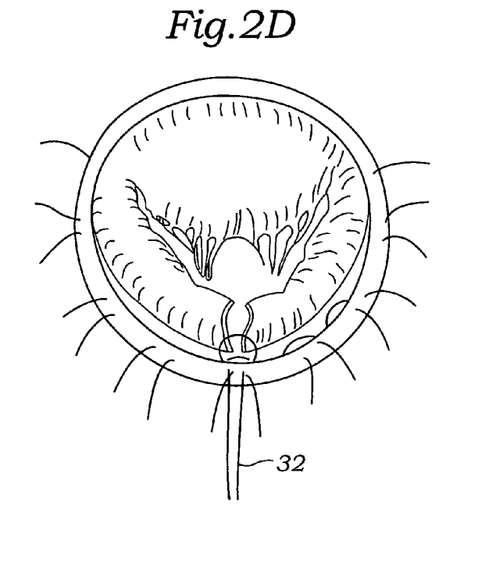
Figure 2E:
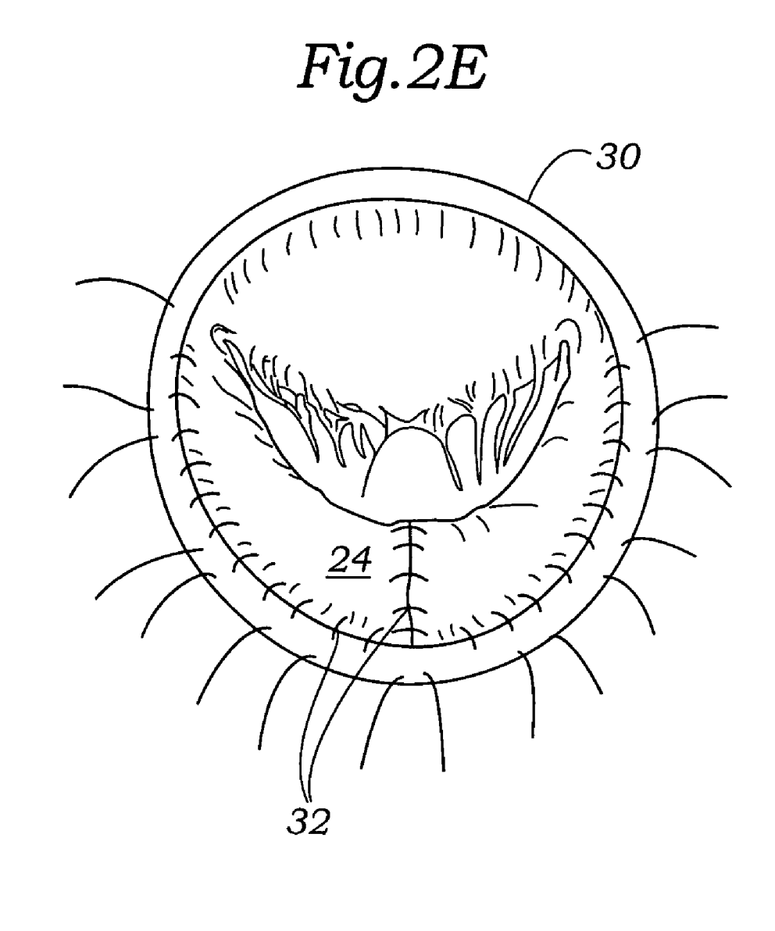
Figure 2F:
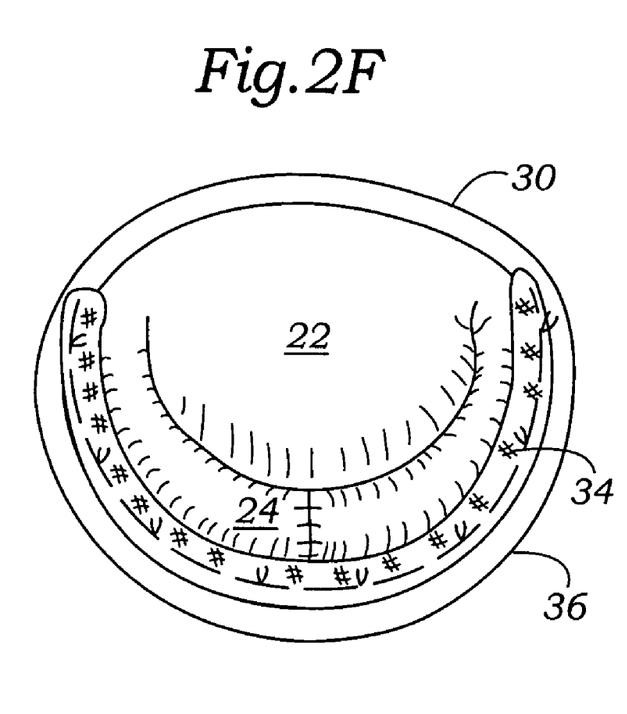

One example of a prior art surgical resection technique for correcting mitral valve prolapse is seen in the sequence of FIGS. 2A-2F. FIG. 2A is a plan view of the mitral valve annulus in which the anterior leaflet 22 and posterior leaflet 24 do not properly coapt in the middle of the annulus. A somewhat smile-shaped gap is seen between the two leaflets. As mentioned above, this condition can result from a number of pathologies, though the particular pathology illustrated is that which often results from Barlow's syndrome. The surgical technique involves resecting a portion of the posterior leaflet 24 by first cutting along the dashed lines 26. FIG. 2B shows the posterior leaflet 24 after the portion indicated in FIG. 2A has been resected and an incision for sliding annuloplasty has been performed FIGS. 2C-2E illustrate a progression of suturing operations in which first stabilizing sutures 28 are passed through the annulus 30 and then a plurality of fixation sutures 32 are used to reapproximate the posterior leaflet 24, thus shortening the posterior leaflet relative to the annulus 30. Finally, in FIG. 2F, an annuloplasty ring 34 has been implanted around the posterior aspect 36 of the annulus 30, generally corresponding to the perimeter of the posterior leaflet 24. A comparison of the size of the annulus 30 in FIGS. 2E and 2F illustrates the effect of the addition of the ring 34. That is, the annulus circumference has been reduced. More importantly though, the leaflets 22, 24 are shown properly coapting without the aforementioned gap.

In early 1990's, Dr. Ottavio Alfieri introduced the concept of edge-to-edge heart valve repair. This repair technique consists of suturing the edges of the leaflets at the site of regurgitation, either at the paracommissural area (eg: A1-P1 segments: para commissural repair) or at the middle of the valve (e.g.: A2-P2 segments: double orifice repair). Three patents disclosing various devices for performing such edge-to-edge procedures are U.S. Pat. No. 6,165,183 to Kuehn, et al., U.S. Pat. No. 6,269,819 to Oz, et al., and U.S. Pat. No. 6,626,930 to Allen, et al. Recently, the edge-to-edge technique has been used in conjunction with annuloplasty procedures for treating the pathology seen with mitral valve prolapse. The underlying bases for these techniques are to eliminate the primary regurgitant area by suturing the leaflet edge and decreasing leaflet mobility, and to correct leaflet redundancy, force coaptation, and restrict leaflet motion.

Despite accepted treatments for correcting mitral valve prolapse, for example Barlow's syndrome, there is a need for a simpler and more effective approach, preferably one that avoids the need for sliding annuloplasty. Sliding annuloplasty adds technical and skill intensive barriers that limit widespread adoption of mitral valve repair.

SUMMARY OF THE INVENTION

The present invention provides a mitral annuloplasty ring comprising a ring body made of a material that will substantially resist distortion when subjected to the stress imparted thereon by an operating human heart. The ring body defines an anterior segment and a posterior portion opposite the anterior segment. Right and left sides are located between the anterior segment and posterior portion. A central flow axis has an upward direction and a downward direction, the downward direction corresponding to the direction of blood flow through the mitral valve annulus when the annuloplasty ring is implanted. The ring body has a modified oval shape with a minor axis extending between the anterior segment and posterior portion, and a major axis extending between the sides. A bow in the posterior portion of the ring body extends both radially outward and axially upward.

In accordance with another aspect, a mitral annuloplasty ring of the present invention comprises a ring body made of a material that will substantially resist distortion when subjected to the stress imparted thereon after implantation in the mitral valve annulus of an operating human heart. The ring body defines a rounded ring body having an anterior segment and a posterior portion. The ring body is oriented about a central flow axis, the flow axis defining an upward direction and a downward direction, the downward direction corresponding to the direction of blood flow through the mitral valve annulus. The posterior portion the ring body bows upward out of a plane perpendicular to the central flow axis and also has a radially outward curve more pronounced than adjacent sections.

In accordance with a still further aspect of the invention, a mitral annuloplasty ring comprises a ring body made of a material that will substantially resist distortion when subjected to the stress imparted thereon after implantation in the mitral valve annulus of an operating human heart, the ring body defines a modified oval-shaped ring body oriented about a central flow axis, the flow axis defining an upward direction and a downward direction, the downward direction corresponding to the direction of blood flow through the mitral valve annulus from the left atrium to the left ventricle, and wherein in plan view as seen along the flow axis the ring body has a major axis perpendicular to a minor axis, the major and minor axes being perpendicular to the flow axis. The ring body having in atrial plan view an anterior segment generally defined between an anterolateral trigone and a posteromedial trigone, and a posterior portion around the remaining periphery of the ring body and between the trigones, the posterior portion being divided into three sequential segments, $P_1$, $P_2$, and $P_3$ starting from the anterolateral trigone and continuing in a counterclockwise direction, the segments generally corresponding to the size of the native posterior leaflet cusps, wherein the minor axis intersects both the anterior segment and the $P_2$ segment of the posterior portion. The ring body lies substantially in a plane defined by the major and minor axes or in a saddle-shaped three-dimensional surface except for the $P_2$ segment of the posterior portion located which is deflected upward and outward with respect to the adjacent sections of the ring body.

In a ring of the present invention, an axial height h of the upward bow or deflection exceeds about 3 mm, more preferably between about 3-10 mm. In atrial plan view as seen along the flow axis, the ring body has a major axis perpendicular to a minor axis, the major and minor axes being perpendicular to the flow axis, and the minor-major dimension ratio is preferably between about 3.3:4 (82.5%) and 4:4 (100%), more preferably about 3.5:4 (87.5%). The bow may be centered about the minor axis and have an angular extent of between about 90-130°, for example about 128°.

The ring body has an anterior segment generally defined between an anterolateral trigone and a posteromedial trigone, and a posterior portion around the remaining periphery of the ring body and between the trigones. The posterior portion is divided into three sequential segments, $P_1$, $P_2$, and $P_3$, starting from the anterolateral trigone and continuing in a counterclockwise direction. Desirably, the bow in the posterior portion is wholly within the middle segment $P_2$ of the posterior portion of the ring. Alternatively, the bow in the posterior portion may be within the middle segment $P_2$ and extend into at least one other segment $P_1$ or $P_3$ of the posterior portion of the ring.

In accordance with a further aspect of the invention, the ring body defines a modified D-shape in atrial plan view with the anterior segment defining a relatively straight side as compared with the posterior portion, and with a minor axis extending between and bisecting the anterior segment and posterior portion and a major axis extending perpendicularly thereto. The major and minor axes are generally perpendicular to the flow axis, and the posterior portion of the ring body has an outward bow more pronounced than adjacent sections and an upward bow from adjacent sections that has an axial height h of between about 3-10 mm. The ring body may be saddle-shaped such that the anterior segment also defines an upward bow from adjacent sections. Desirably, the outward bow has an angular extent of between 90-130°, and the outward bow includes an outward bulge that has a smaller radius of curvature than adjacent sections and spans an angular extent of between about 80-90°. Preferably, the upward bow in the posterior portion has an angular extent approximately equal to the outward bulge.

The present invention further provides a method of correcting mitral valve prolapse wherein a posterior leaflet of the mitral valve is causing mitral regurgitation. The method includes providing an annuloplasty ring with a ring body having an upwardly and outwardly bowed posterior portion, and a suture-permeable exterior on the ring body for securing the annuloplasty ring to the mitral annulus. The method includes delivering the annuloplasty ring to the mitral annulus and securing the annuloplasty ring to the mitral annulus using the suture-permeable exterior such that the posterior portion pulls the periphery of the posterior leaflet of the mitral valve outward and upward and reduces the mitral regurgitation.

A mitral annuloplasty ring of the present invention may also be defined by a ring body that has a modified D-shape in atrial plan view with an anterior segment defining a relatively straight side as compared with a posterior portion. A minor axis extends between and bisects the anterior segment and posterior portion, and a major axis extends perpendicularly thereto. The major and minor axes are generally perpendicular to the flow axis, and the posterior portion of the ring body has an outward bow that creates a minor axis to major axis dimension ratio of between about 3.3:4 (82.5%) and 4:4 (100%). Desirably, the ring body further includes an upward bow in the posterior portion.

In the modified D-shaped annuloplasty ring, the axial height h of the upward bow is preferably between about 11%-28% of the major axis dimension. In absolute terms, the axial height h of the bow is between about 3-10 mm. The outward bow may have an angular extent of between 90-130°. In a preferred embodiment, the minor axis to major axis dimension ratio is between about 3.44:4 (86%) and 3.6:4 (90%). The ring body may define an outward bulge in the outward bow of the posterior portion that has a smaller radius of curvature than adjacent sections. Desirably, the sections adjacent the outward bulge are relatively straight. In ring bodies that have an upward bow, it desirably has an angular extent approximately equal to the outward bulge. More particularly, the outward bow preferably spans an angular extent of between about 90-130°, and the outward bulge spans an angular extent of between about 80-90°. In a preferred embodiment, the ring body defines a continuous, closed periphery.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention provides a novel annuloplasty ring for correcting pathologies associated with mitral valve prolapse, also known by a number of other names given above, including Barlow's syndrome. With this pathology, the mitral valve leaflets are distended (i.e., stretched, lengthened, swelled, thickened) or in general have become loose and floppy such that they do not properly coapt. In contrast to prior repair techniques, the annuloplasty ring of the present invention reduces or eliminates the need for a sliding annuloplasty. Furthermore, instead of attempting to constrict the mitral annulus by the addition of an annuloplasty ring that is under-sized with respect to the existing annulus, the present invention accommodates the excess material of the leaflets by providing a larger support ring than has previously been utilized. Typical annuloplasty support rings have a long or major dimension and a short or minor dimension, with the conventional ratio of the minor to major dimension being approximately 3:4 (75%). The present invention provides an annuloplasty ring that has a significantly increased minor to major dimension ratio of between about 3.3:4 (82.5%) and 4:4 (100%).

Annuloplasty rings of the present invention are desirably made of material(s) that will substantially resist distortion when subjected to the stress imparted thereon by the mitral valve annulus of an operating human heart. In this sense, "distortion" means substantial permanent deformation from a predetermined or manufactured shape; the opposite concept of which is "elastic" meaning the ability to recover the ring shape in the absence of an external force. Furthermore, the posterior aspect of the annuloplasty rings is relatively inflexible, in contrast to a ring made substantially of silicone. A number of materials can be utilized that will perform this function, including various bio-compatible polymers and metals and/or alloys. Certain polyesters that resist distortion and also rapid degradation within the body may be used (a material that degrades more slowly, however, may provide the required initial support). In a preferred embodiment, at least an inner core or body of the annuloplasty ring of the present invention is made of a suitable metal, such as titanium or its alloys, or ELGILOY made by Elgiloy, L. P. of Elgin, Ill., U.S.A. The core or ring body may be one piece, or may include a plurality of concentric or otherwise cooperating elements. The addition of a silicone tube or band around the ring body and a suture-permeable fabric on the exterior of the ring are also contemplated.

In a preferred embodiment, the annuloplasty ring of the present invention comprises a continuous ring body made of a titanium alloy. A tubular sleeve or outer band of silicone around the ring body helps conform tissue to the ring after implantation. Finally, a tubular fabric covering around the silicone sleeve provides an anchoring platform for sutures or other attachment devices such as staples. The fabric covering is typically Dacron (polyethylene terephthalate). The tubular fabric covering around the silicone sleeve provide an interface for securing the annuloplasty ring to the mitral annulus, although other interfaces are contemplated. For example, rings having outward hooks or barbs are known in the art.

Figures 3A, 3B:
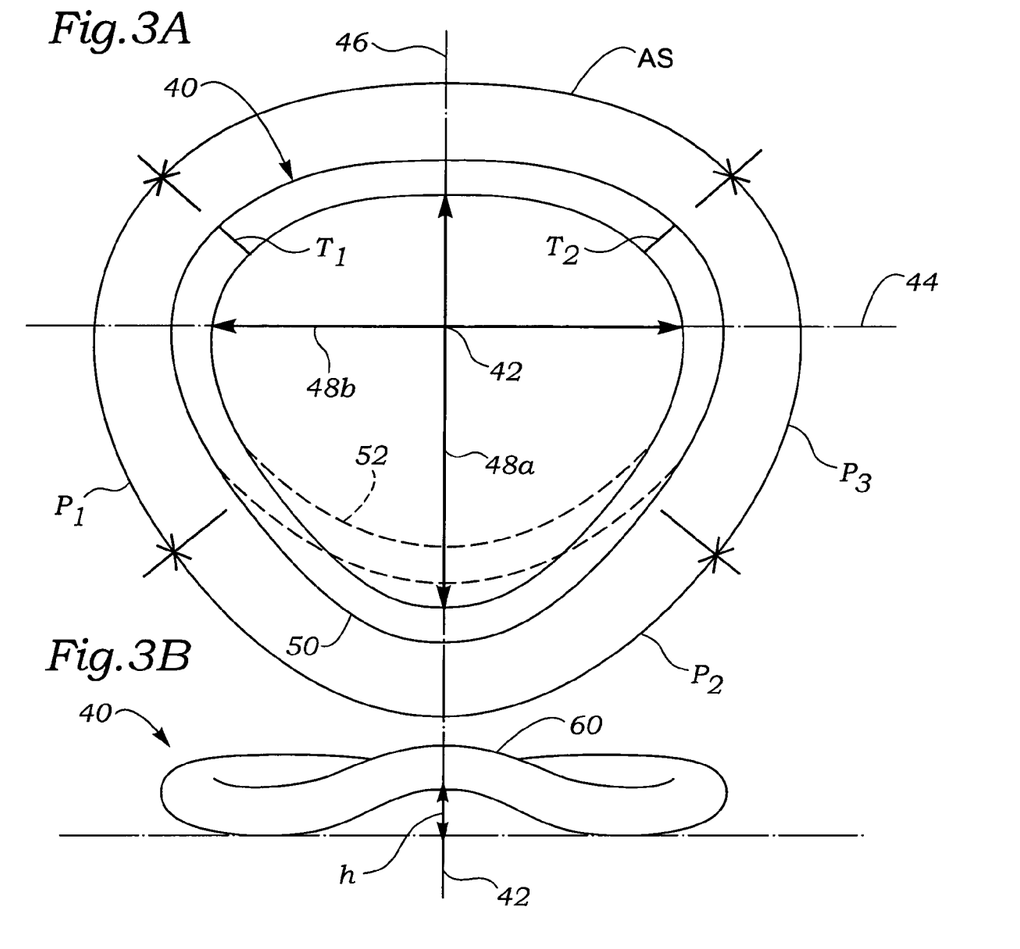
FIGS. 3A-3B are top plan and posterior elevational views, respectively, of a mitral annuloplasty ring of the present invention having an outward and upward posterior bow.

With reference now to FIGS. 3A and 3B, an exemplary mitral annuloplasty ring 40 is shown in plan and posterior elevational views, respectively. These views illustrate the completed ring so that a fabric covering is all that is visible. An exemplary ring body will be described below with respect to FIGS. 6-10, though it should be understood that the shape of the completed ring follows closely the shape of the inner ring body which provides its primary structural support.

The annuloplasty ring 40 has a modified oval shape (closed) in plan view and is oriented about a central flow axis 42. The flow axis 42 defines an upward direction and a downward direction, corresponding to the top and bottom of the page relative to the ring 40 as seen in FIG. 3B. The downward direction corresponds to the direction of blood flow through the mitral valve annulus from the left atrium to the left ventricle, such that up is synonymous with the inflow direction and down the synonymous with the outflow direction of the valve. Looking along the flow axis 42 in FIG. 3A, the ring 40 has a major axis 44 perpendicular to a minor axis 46, the major and minor axes being perpendicular to the flow axis. It should also be understood that the "flow axis" here may not necessarily be the center of the volumetric flow through the annulus, but is instead orthogonal to the major and minor axes 44, 46, and therefore defines the gross direction of flow.

A minor axis dimension 48a is shown extending across the interior of the ring 40 in plan view. Likewise, a major axis dimension 48b is shown extending horizontally across the interior of the ring. Desirably, the ratio of the minor axis dimension 48a to the major axis dimension 48b is about 3.5:4 (87.5%).

For purpose of further definition, a pair of trigone markers $T_1$ and $T_2$ are shown on the ring 40 corresponding to the approximate location of the fibrous trigones of the mitral annulus when the ring is implanted. An anterior segment extends around the upper portion of the ring 40 in FIG. 3A between the trigone markers $T_1$, $T_2$. When the ring 40 is implanted, the anterior segment will coincide with the anterior aspect of the mitral annulus. The anterior segment is shown planar, though it may be upwardly curved or bowed to better conform to the anterior aspect of the native annulus, as will be shown below in FIGS. 6-10 with respect to an exemplary ring body.

The remainder of the ring 40 aside from the anterior segment between the trigone markers $T_1$, $T_2$ will be termed the posterior portion, and is shown broken up into three sequential segments denoted $P_1$, $P_2$, and $P_3$ (in series counter-clockwise from the first trigone marker $T_1$). The precise angular dividing line between these three segments is not standardized, though they are intended to generally correspond to the three visible cusps of the posterior leaflet of the mitral valve. In an exemplary embodiment, the three segments are approximately equal in angular dimension, and the middle segment $P_2$ is symmetric about the minor axis 46. It should be noted that annuloplasty rings are shaped and marked so as to orientation-specific, such that the anterior segment is adapted to be implanted against the anterior aspect of the mitral annulus, and the same with the posterior portion.

The annuloplasty ring 40 has a modified D- or oval shape in plan view because of an outward bow 50 within the middle segment $P_2$ of the posterior portion of the ring. Stated another way, the middle segment $P_2$ of the posterior portion of the ring has an outward curve (convexity) more pronounced than adjacent sections (which may also be convex or relatively straight). The outward bow 50 thus bulges outward from the adjacent sections. A dashed outline 52 of a conventional 3:4 ratio "D-shaped" annuloplasty ring is shown to illustrate the outward bow 50 of the present ring 40. For purpose of reference, a conventional 3:4 ratio "D-shaped" annuloplasty ring means the relaxed shape of a Carpentier-Edwards Physio® annuloplasty ring available from Edwards Lifesoiences of Irvine, Calif. (www.edwards.com).

As mentioned above, the outward bow 50 preferably results in a minor-major axis dimensional ratio of 3.5:4 (87.5%), although the present invention encompasses rings having an outward bow 50 that produces ratios of between about 3.3:4 (82.5%) and 4:4 (100%).

It is important to note that although the minor axis dimension 48a increases relative to conventional D-shaped rings (i.e., dashed outline 52), the major axis dimension 48b will remain substantially the same. Furthermore, although the outward bow 50 is shown within the middle segment $P_2$ of the posterior portion of the ring, the entire posterior portion below the major axis 44 may be affected. That is, the outward bow 50 may extend into one or both of the first and third segments $P_1$ and $P_3$ of the posterior portion. In a preferred embodiment, however, the annuloplasty ring 40 only diverges from a conventional oval- or D-shaped ring (such as the Carpentier-Edwards Physio® ring) within the middle segment $P_2$. In an exemplary embodiment, the angular extent of the outward bow 50 as measured about the central axis 42 is between 90-130°, and more preferably about 128°.

In conjunction with the outward bow 50, the annuloplasty ring 40 also includes an upward bow 60 seen in FIG. 3B. The term "upward bow" refers to either an upward divergence from a planar ring, or an upward divergence from a so-called "saddle-shaped" ring. Therefore, the present invention encompasses both planar and saddle-shaped rings having an outward and upward posterior bow.

A height h of the upward bow 60 is indicated in FIG. 3B and desirably exceeds about 3 mm, preferably more than about 4 mm, and most preferably between about 3-10 mm. The upward bow 60 may or may not be formed in the ring 40 around the same angular extent as the outward bow 50. In a preferred embodiment, the outward bow 50 spans a smaller angular extent than the upward bow 60, although they may start and end at the same location around the ring 40. Likewise, both the outward bow 50 and upward bow 60 are desirably centered along the minor axis 46, although one or both may be asymmetrically offset.

Figure 4:
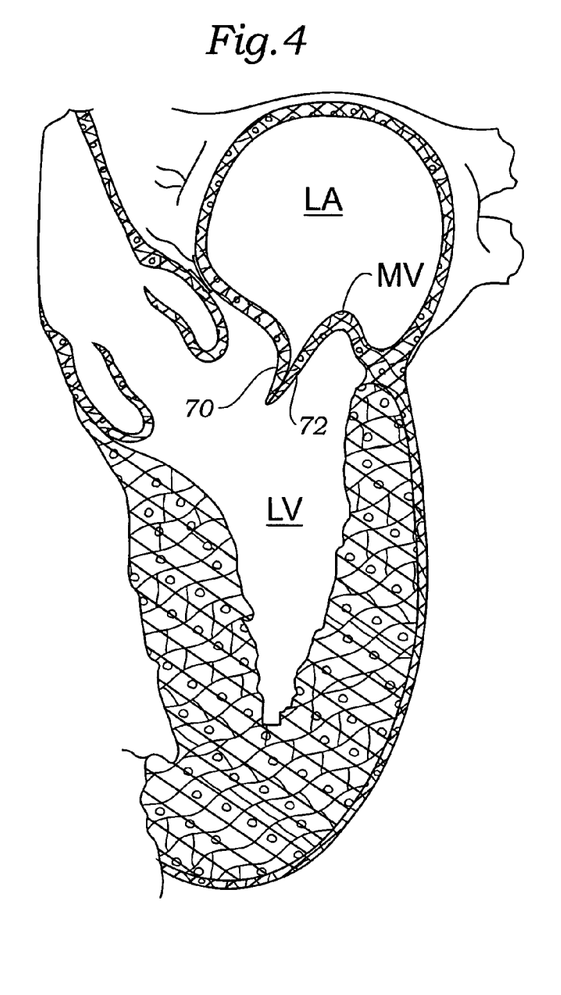
FIG. 4 is an enlarged sectional view of the left ventricle of a human heart illustrating another possible configuration of a distended mitral valve leaflets seen with mitral valve prolapse.

FIG. 4 is a further sectional illustration of the left ventricle LV showing a different configuration of the leaflets resulting from mitral valve prolapse than that shown in FIG. 1. In this figure, the chordae tendinae are not shown for clarity. The anterior leaflet 70 is shown relatively normal, while the other leaflet 72 is prolapsed in that it is bunched or otherwise distended. In this condition, the leaflets 70, 72 may not fully coapt, resulting in mitral regurgitation.

Figure 5:
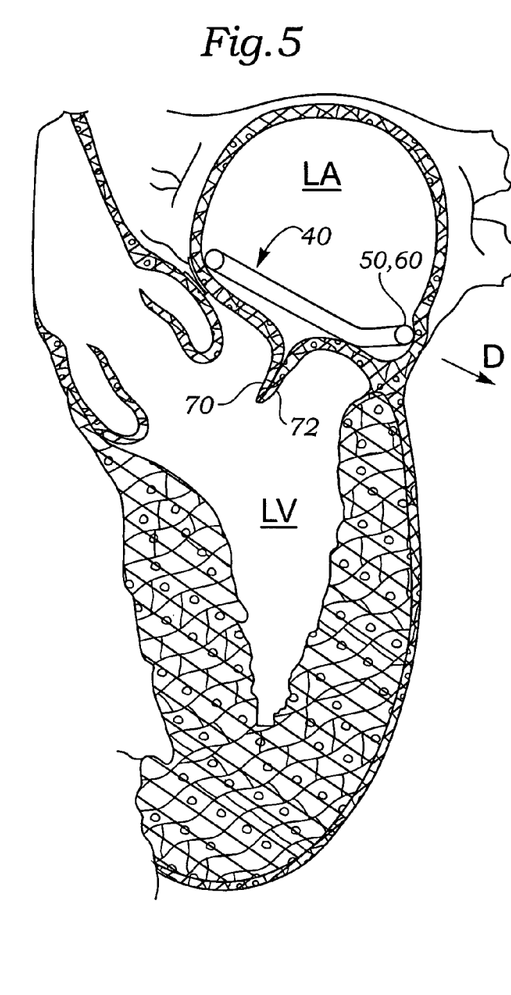
FIG. 5 is an enlarged sectional view similar to FIG. 4 illustrating implantation of a mitral annuloplasty ring of the present invention that helps insure leaflet coaptation.

FIG. 5 illustrates the implantation of the annuloplasty ring 40 in the mitral annulus to correct the condition of FIG. 4. The outward and upward bow 50, 60 of the ring 40 is shown located at the posterior aspect of the annulus. The shape of the ring 40 on the posterior side causes a displacement D of the posterior aspect of the mitral annulus, and helps reduce the "slack" existent in the posterior leaflet. As a result, the leaflets 70, 72 are shown properly coapting to substantially eliminate regurgitation.

Figures 6A, 6B, 7, 8:
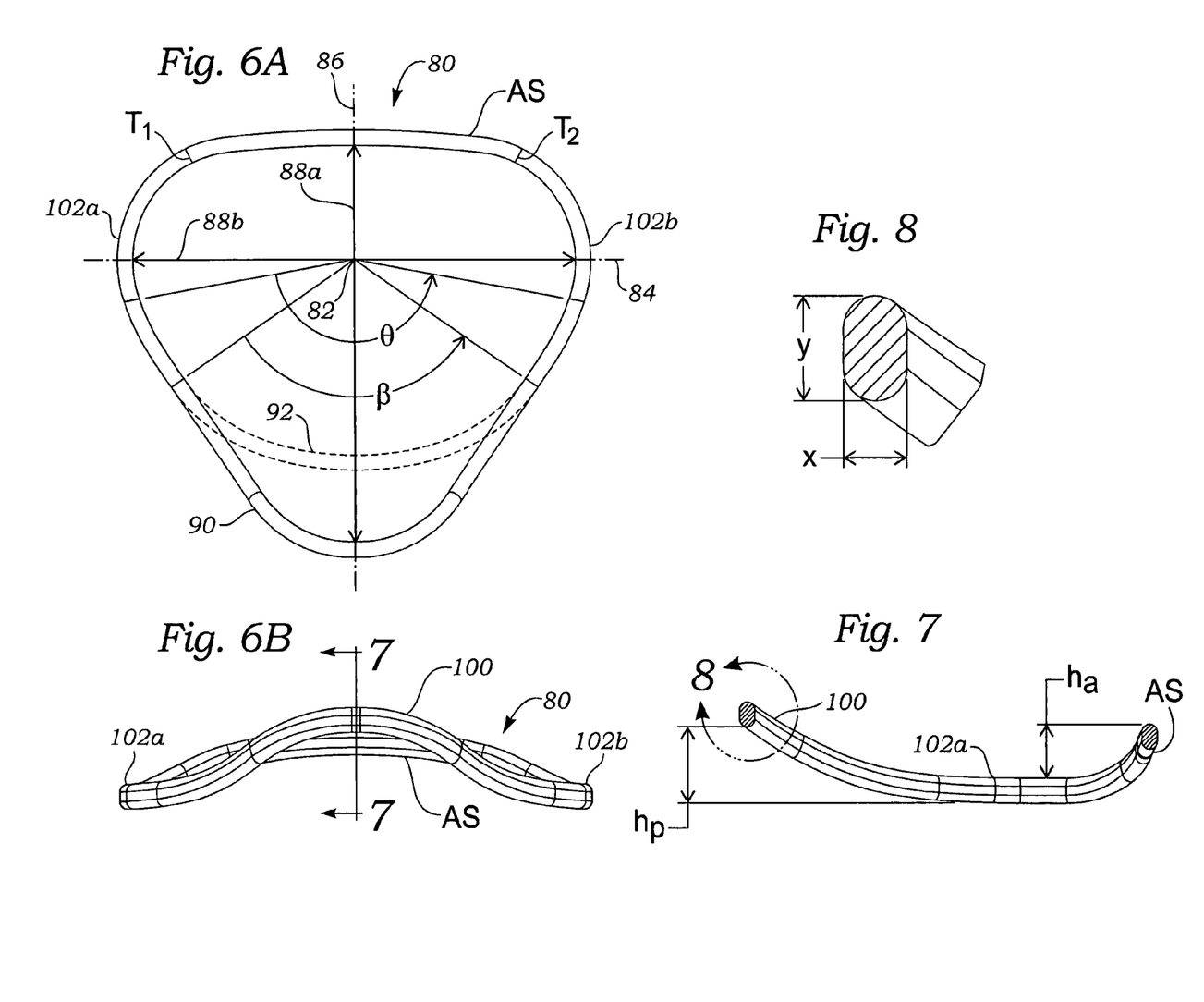
FIGS. 6A and 6B are top plan and posterior elevational views, respectively, of an exemplary annuloplasty ring body forming the primary structural component of the annuloplasty ring of the present invention.
FIG. 7 is a vertical sectional view through the exemplary annuloplasty ring body taken along a line of symmetry 7-7 seen in FIG. 6B.
FIG. 8 is an enlarged view of the radial section through one side of the annuloplasty ring body seen in the encircled area in FIG. 7.

With reference now to FIGS. 6A and 6B, an exemplary mitral annuloplasty ring body 80 is shown in plan and posterior elevational views, respectively. These views therefore omit a silicone sleeve and fabric covering. It should be understood that the shape of the completed ring 40 as seen in FIG. 3A follows closely the shape of the inner ring body 80 which provides its primary structural support.

The annuloplasty ring body 80 has a modified oval shape in plan view and is oriented about a central flow axis 82. The flow axis 82 defines an upward direction and a downward direction, corresponding to the top and bottom of the page relative to the ring body 80 as seen in FIG. 6B. Looking along the flow axis 82 in FIG. 6A, the ring body 80 has a major axis 84 perpendicular to a minor axis 86, the major and minor axes being orthogonal to the flow axis 82.

For purpose of further definition, a pair of trigone markers $T_1$ and $T_2$ are shown on the ring body 80 corresponding to the approximate location of the fibrous trigones of the mitral annulus when the ring is implanted. An anterior segment AS extends around the upper portion of the ring body 80 in FIG. 6A between the trigone markers $T_1$, $T_2$. The remainder of the ring body 80 aside from the anterior segment AS between the trigone markers $T_1$, $T_2$ will be termed the "posterior portion." The surgeon will implant the ring such that the anterior segment AS of the ring body 80 will register with the anterior aspect or leaflet of the mitral annulus, and the posterior portion will register with the posterior aspect or leaflet. Again, it is important to understand that annuloplasty rings such as those of the present invention are not rotatable within the annulus. That is, a particular orientation is indicated on the packaging, or by reference to the trigone markers $T_1$, $T_2$, and the ring is constructed to be specific to that orientation. A surgeon would not, for instance, implant the ring with the anterior segment AS adjacent the posterior aspect of the mitral annulus, and vice versa.

With regard still to FIG. 6A, a minor axis dimension 88a extends vertically across the interior of the ring body 80 in plan view. Likewise, a major axis dimension 88b extends horizontally across the interior of the ring body. Desirably, the ratio of the minor axis dimension 88a to the major axis dimension 88b is about 3.5:4 (87.5%), although the present invention provides a ring having an outward bow 90 that may create a minor axis/major axis ratio of between about 3.3:4 (82.5%) and 4:4 (100%).

The extent of the outward bow 90 of the ring body 80 has been discussed above in general terms. However, it is important to understand that the major and minor axes can be measured at different points on the ring body 80, and with respect to the completed ring 40 as seen in FIG. 3A. The completed ring 40 includes the inner ring body 80, a surrounding sleeve or band of silicone, and a fabric covering therearound. Therefore, the major and minor axes can be measured to the inside or outside dimensions of the ring body, and likewise with respect to the completed ring.

Figure 9A:
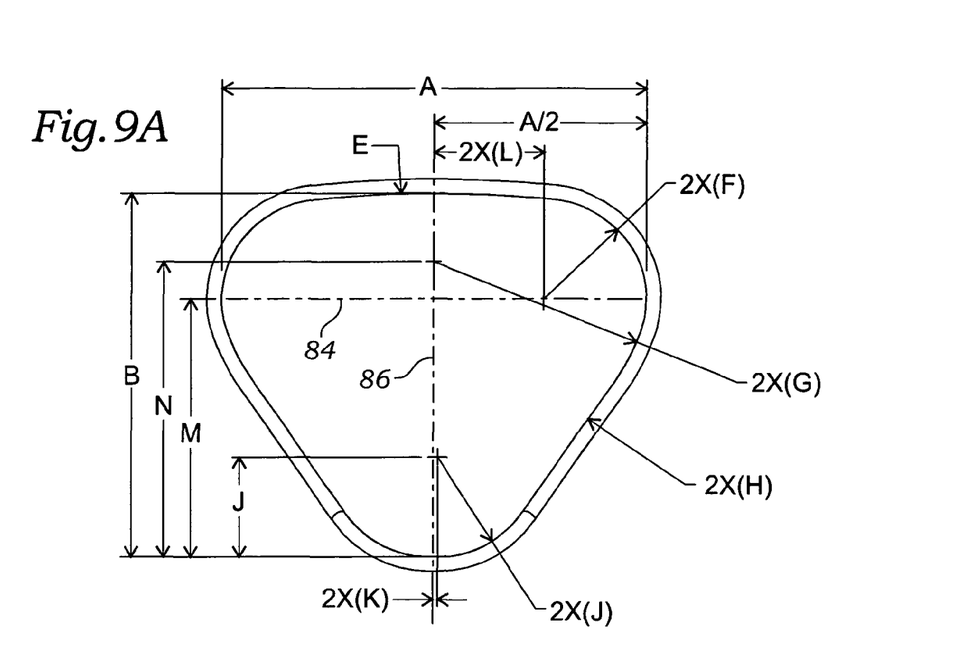
FIGS. 9A-9C are top plan, posterior elevational, and vertical sectional views similar to FIGS. 6A-6B and 7 indicating a number of dimensional parameters.

The following table indicates percentage ratios of the minor axis to the major axis as measured across several different landmarks for the six different exemplary rings, and also gives the actual values of the major and minor axes as measured across the interior of the ring body 80 (dimensions A and B in FIG. 9A).

| Ring size (mm) | Across ring 40 OD | Across ring 40 ID | Across ring body 80 ID | Major axis (mm) | Minor Axis (mm) |
|---|---|---|---|---|---|
| 26 | 90.0% | 86.7% | 87.5% | 26.0 | 22.8 |
| 28 | 89.9% | 86.8% | 87.5% | 28.0 | 24.5 |
| 30 | 89.8% | 86.8% | 87.5% | 30.0 | 26.2 |
| 32 | 89.6% | 86.9% | 87.5% | 32.0 | 28.0 |
| 34 | 89.5% | 86.9% | 87.5% | 34.0 | 29.7 |
| 36 | 89.4% | 86.9% | 87.5% | 36.0 | 31.5 |

Again, the ratio of the minor axis to the major axis desirably falls within a range of 3.3:4 to 4:4 (82.5%-100%), more preferably between about 3.44:4 to 3.6:4 (86%-90%), and most preferably 3.5:4 (87.5%). The preceding table also indicates that the dimensional parameters set forth herein with respect to the ring body 80 correspond closely with those of the completed ring 40, and the corollary is also true; that any dimensional ranges, preferred values or ratios set forth for the ring 40 generally apply to the ring body 80.

As stated above, the annuloplasty ring body 80 has a modified oval shape in plan view (FIG. 6A) because of the outward bow 90 within the middle of the posterior portion of the ring. Stated another way, the middle of the posterior portion of the ring body 80 has an outward curve (convexity) more pronounced than adjacent sections (which may also be convex or relatively straight). A dashed outline 92 of a conventional 3:4 ratio "D-shaped" annuloplasty ring is shown to illustrate the more pronounced outward bow 90 of the present ring body 80.

It is important to note that although the minor axis dimension 88a increases relative to conventional D-shaped rings (i.e., dashed outline 92), the major axis dimension 88b will remain substantially the same. Furthermore, although the outward bow 90 is shown centered within the middle of the posterior portion of the ring, the entire posterior portion below the major axis 84 may be affected. That is, the outward bow 90 may extend into one or both of the first and third segments $P_1$ and $P_3$ of the posterior portion, as was defined with respect to FIG. 3A. In a preferred embodiment, however, the annuloplasty ring body 80 only diverges from a conventional oval- or D-shaped ring (such as the Carpentier-Edwards Physio® ring) within the middle segment $P_2$. In an exemplary embodiment, the angular extent β of the outward bow 90 as measured about the central axis 82 is between 90-130°, and more preferably about 128°.

The exemplary ring body 80 of the present invention further includes an upward bow 100 seen in FIGS. 6B and 7. Again, the term "upward bow" refers to either an upward divergence from a planar ring, or an upward divergence from a so-called "saddle-shaped" ring. Therefore, the present invention encompasses both planar and saddle-shaped rings having an outward and upward posterior bow. In the illustrated embodiment, the ring body 80 exhibits right and left sides 102a, 102b located approximately adjacent the anterior segment AS that, as seen in FIG. 6B, defined the lowermost portions of the ring body. That is, if the ring body 80 is placed on a flat base surface, the right and left sides 102a, 102b rest on the base surface while the anterior segment AS and posterior portion rise upward from the base surface. In this context, therefore, the upward bow 100 rises up from the adjacent right and left sides 102a, 102b.

The upward posterior bow 100 rises to a height $h_p$ as indicated in FIG. 6B desirably exceeding about 3 mm, preferably more than about 4 mm, and most preferably between about 3-10 mm. Another way to express the magnitude of the upward bow 100 is as a percentage of the major axis dimension 88b. In this context, the upward bow 100 is desirably between about 11%-28%, and more preferably about 17%, of the major axis dimension 88b.

The upward bow 100 may or may not be formed in the ring 40 around the same angular extent as the outward bow 90. In a preferred embodiment, the upward bow 100 spans a peripheral extent of the ring body 80 that is larger than the outward bow 90. For example, the upward bow 100 may be centered about the minor axis 86 and commence at symmetric locations on both sides of the posterior portion just below the major axis 84, as indicated in FIG. 6A, so as to span an angle θ which is desirably between about 130° and 180°. More particularly the angle θ is about 175°. Alternatively, the upward bow 100 may be asymmetric about the minor axis 86 and extend farther around the ring into either the first and third segments $P_1$ and $P_3$ of the posterior portion, as was defined with respect to FIG. 3A.

As seen in FIGS. 6B and 7, the anterior segment AS is shown upwardly curved or bowed to better conform to the anterior aspect of the native annulus. The height $h_a$ of the anterior segment AS is indicated in FIG. 7, and desirably ranges between about 3-5 mm as measured from the adjacent right and left sides 102a, 102b. Another way to express the magnitude of the height $h_a$ of the anterior segment AS is as a percentage of the major axis dimension 88b. In this context, the height $h_a$ is desirably between about 11%-14%, and more preferably about 12%, of the major axis dimension 88b. Again, rings constructed in accordance with the present invention may have a flat or planar anterior segment AS, or may be upwardly bowed as shown. This upward curvature has been adopted in certain more rigid rings of the prior art to more faithfully conform to the upward contour at the anterior aspect of the mitral annulus. In alternative configurations, the anterior segment AS may be planar but more flexible than the remainder of the ring, or the ring may be discontinuous in a so-called "C-shape" with a gap at the anterior segment.

The present invention contemplates an annuloplasty ring with an upward and outward posterior bow, but also with particular dimensions, ratios, and contours to optimize performance. One such dimensional configuration is the cross-sectional shape. FIG. 8 illustrates a radial cross-section through the highest point in the posterior portion of the ring body 80, at the center of the upward bow 100. As shown, the cross-section has a vertically-oriented oval configuration with a radial dimension x and a greater axial dimension y. This configuration is desirable as it provides sufficient strength (as required by a stress analysis) but minimizes the radial thickness (x dimension) so that a relatively robust sewing band around the periphery may be utilized without compromising orifice area. A thicker sewing band facilitates implant. The particular shape shown, a vertically-oriented oval, is believed most desirable because of its rounded contours and consequent lack of stress risers. In a preferred embodiment, the cross-section of the ring body 80 is constant around its periphery, although a varying cross-section to vary the flexibility around the ring body is also contemplated. In one exemplary embodiment, the radial dimension x is between about 60% to 70% of the axial dimension y. Additionally, the top and bottom rounded ends of the cross-section are desirably complete semi-circles having a diameter that equals the radial dimension x. For example, x=0.049 inches (1.24 mm) and y=0.079 inches (2.00 mm).

As mentioned above, the illustrated ring body 80 may be constructed of a single, homogenous length of a relatively rigid material such as titanium. As such, the ring body 80 will substantially resist distortion when subjected to the stress imparted thereon by the mitral valve annulus of an operating human heart. It should be understood that less rigid materials may provide some radial bending flexibility for the ring to accommodate in and out movement of the annulus during systolic-diastolic cycles. For instance, a polymer ring formed with the cross-section shown in FIG. 8 may flex radially, though it will be stiffer axially. Or, the ring body 80 may be formed from a plurality of concentric radially thin bands of a more rigid material such as titanium, which reduces radial rigidity without compromising axial strength. Desirably, the ring body 80 preferably possesses a higher vertical area moment of inertia than its horizontal area moment of inertia, thus resulting in greater bending flexibility about the flow axis (i.e., in and out flexibility) than about radial axes (i.e., up and down flexibility). This construction helps preserves the integrity of the upward bow 100, which is important to correct the pathology that led to mitral valve prolapse. In all cases, however, the ring materials are elastic and will substantially resist distortion of the preferred (or manufactured) ring shape when subjected to annulus forces.

Figure 9B:
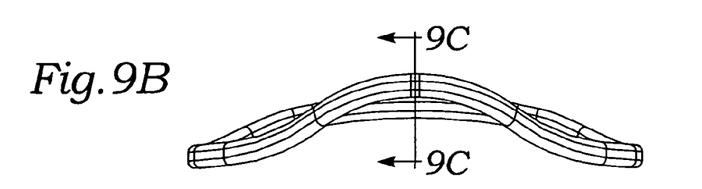
Figure 9C:
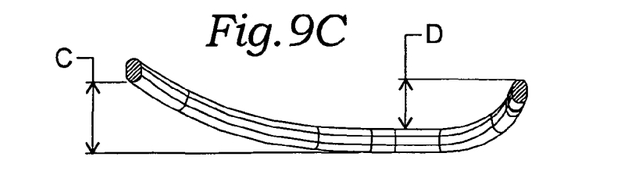

FIGS. 9A-9C illustrate further preferred dimensions and contours for the exemplary ring body 80. As is common, annuloplasty rings are sized in even 2 mm increments, and various dimensional parameters indicated by letters (A, B, etc.) are generally proportional for rings between about 24 and 40 mm. However, the cross-section of each of these differently sized rings desirably remains the same, as discussed above with respect to FIG. 8, and do not become proportionally larger with larger rings, though a set of rings with proportionally sized cross-sections is entirely feasible.

The reader should also note the particular contours of the ring body periphery as seen in the plan view of FIG. 9A, and also with reference to the features shown in FIG. 6A. Beginning at the top, the anterior aspect AS has a very slight outward curvature (convexity) indicated by the radius E. The upper corners of the ring body near the trigone markers $T_1$, $T_2$ (see FIG. 6A) exhibit a curvature having a radius F that is centered about a point on the major axis 84 a distance L from the minor axis 86, approximately halfway to the ring body 80. The extent of the corner curvature (radius F) is approximately 90°. The corners terminate at the plane of the major axis 84, which plane is desirably spaced a distance M from the posterior apex that is approximately 71% of the interior dimension B of the minor axis 86.

Small convex segments having a radius G (centered on the minor axis 86 a distance N from the posterior apex) that have a lesser curvature than the upper corners lead to relatively straight side segments having a very slight inward (concave) curvature with a radius H. The right and left sides 102a, 102b of the ring that are indicated in FIG. 6A comprise part of the upper corners (radius F) and the adjacent small convex segments (radius G). The relatively straight sections indicated by the radius H on both sides of the ring body define the beginning of the outward bow 90, and make up a majority of the first and third segments $P_1$ and $P_3$ of the posterior portion (see FIG. 3A). The straight sections are illustrated as slightly concave, though they may be straight or slightly convex as well. These sections essentially narrow the ring body 80 on the posterior side so that the outward bow 90 is isolated in the middle or $P_2$ segment, rather than affecting the adjacent $P_1$ or $P_3$ segments. That is, rather than comprising a smooth, relatively gradual change of curvature, the outward bow 90 is formed by a bulge centered in the posterior portion that has a smaller radius of curvature than the adjacent sections.

Finally, the outermost posterior apex straddling the minor axis 86 has a radius of J that is desirably about the same as the radius F near the trigone markers $T_1$, $T_2$. It should be noted that the centers of curvature of the two sides of the outermost posterior apex are slightly offset from the minor axis 86, as indicated, which slightly widens or flattens the posterior point of the ring body relative to a constant curvature. This outermost curved portion spans an angular or peripheral extent of between about 80-90° within the total outward bow of about 128°.

FIG. 9B again illustrates the particular contours of the upward bow 100. It should be noted that the upward bow 100 has gradual segments adjacent the sides 102a, 102b and then a more dramatic mid-segment. As mentioned above, the entire angular extent of the upward bow 100 is approximately 175° symmetric about the minor axis 86. The more dramatic mid-segment spans an angular extent approximately 128°, and in this respect corresponds approximately to the preferred peripheral span of the outward radial bow 90.

The annuloplasty ring of the present invention is believed to more effectively correct the pathology seen with mitral valve prolapse because it accommodates the longer and/or thicker leaflets instead of attempting to perform a sliding annuloplasty, which is more surgical art than an exact science. The combination of the outward bow and the upward bow on the posterior side of the ring is believed to provide rigid support for the posterior leaflet from which it can more effectively coapt with the anterior leaflet. The annuloplasty ring essentially "pulls" the posterior leaflet outward and upward which reduces its slack or floppiness. Furthermore, the ring should pull the coaptation point outward and upward and away from the LVOT. This should reduce the incidence of SAM and LVOT obstruction and mitral regurgitation post-repair.

While the invention has been described in its preferred embodiments, it is to be understood that the words which have been used are words of description and not of limitation. Therefore, changes may be made within the appended claims without departing from the true scope of the invention.

What is claimed is:

1. A method of correcting mitral valve prolapse wherein a posterior leaflet of the mitral valve is causing mitral regurgitation, comprising:
   providing an annuloplasty ring having:
      a rounded ring body arranged in atrial plan view around a flow axis defining an upward direction and a downward direction, the downward direction corresponding to the direction of blood flow through the mitral valve annulus when the annuloplasty ring is implanted;
      an anterior segment extending between two trigones and adapted to be implanted against the anterior aspect of the mitral annulus;
      a posterior portion opposite the anterior segment adapted to be implanted against the posterior aspect of the mitral annulus, wherein the posterior portion defines a bow that curves both outward and upward relative to adjacent sections of the ring, the bow being centered in the posterior portion,
      wherein the ring body defines a modified D-shape in atrial plan view with the anterior segment defining a relatively straight side as compared with the posterior portion, and with a minor axis extending between and bisecting the anterior segment and posterior portion and a major axis extending perpendicularly thereto, the major and minor axes being generally perpendicular to the flow axis, and wherein the outward bow of the posterior portion creates a minor axis to major axis dimension ratio of between 3.44:4 (86%) and 3.6:4 (90%); and
      a suture-permeable exterior on the ring body for securing the annuloplasty ring to the mitral annulus;
   delivering the annuloplasty ring to the mitral annulus; and
   securing the annuloplasty ring to the mitral annulus using the suture-permeable exterior such that the posterior portion pulls the periphery of the posterior leaflet of the mitral valve outward and upward and reduces the mitral regurgitation.

2. The method of claim 1, wherein an axial height h of the upward bow of the posterior portion is between about 11%-28% of the major axis dimension.

3. The method of claim 1, wherein an axial height h of the upward bow of the posterior portion is between about 3-10 mm.

4. A mitral annuloplasty ring comprising a ring body arranged around a flow axis having an upward direction and a downward direction, the downward direction corresponding to the direction of blood flow through the mitral valve annulus when the annuloplasty ring is implanted, the ring body comprising:
   an anterior segment generally defined between two trigones and adapted to be implanted against the anterior aspect of the mitral annulus;
   a posterior portion opposite the anterior segment adapted to be implanted against the posterior aspect of the mitral annulus, and
   wherein the ring body defines a modified D-shape in atrial plan view with the anterior segment defining a relatively straight side as compared with the posterior portion that includes an outward curve, and with a minor axis extending between and bisecting the anterior segment and posterior portion and a major axis extending perpendicularly thereto, the major and minor axes being generally perpendicular to the flow axis, and wherein the posterior portion of the ring body has an outward bulge centered in the posterior portion that is radially outwardly curved more pronounced than adjacent sections of the posterior portion and creates a minor axis to major axis dimension ratio of between 3.44:4 (86%) and 3.6:4 (90%), and wherein the sections adjacent the outward bulge are relatively straight.

5. The mitral annuloplasty ring of claim 4, wherein the ring body further includes an upward bow in the posterior portion.

6. The mitral annuloplasty ring of claim 5, wherein an axial height h of the upward bow is between about 11%-28% of the major axis dimension.

7. The mitral annuloplasty ring of claim 6, wherein the axial height h of the upward bow is between about 3-10 mm.

8. The mitral annuloplasty ring of claim 4, wherein the outward bulge has an angular extent of between 80-90°.

9. The mitral annuloplasty ring of claim 4, wherein the sections adjacent the outward bulge each have a slightly concave curvature.

10. The mitral annuloplasty ring of claim 4, wherein the ring body further includes an upward bow in the posterior portion that has an angular extent approximately equal to the outward bulge.

11. The mitral annuloplasty ring of claim 4, wherein the ring body defines a continuous, closed periphery.

12. The mitral annuloplasty ring of claim 4, wherein the ring body is saddle-shaped such that the anterior segment also defines an upward bow from adjacent sections.

13. The mitral annuloplasty ring of claim 4, wherein the ring body further includes an upward bow in the posterior portion that has an angular extent greater than that of the outward bulge.

14. A mitral annuloplasty ring comprising a ring body arranged around a flow axis having an upward direction and a downward direction, the downward direction corresponding to the direction of blood flow through the mitral valve annulus when the annuloplasty ring is implanted, the ring body comprising:
   an anterior segment generally defined between two trigones and adapted to be implanted against the anterior aspect of the mitral annulus;
   a posterior portion opposite the anterior segment adapted to be implanted against the posterior aspect of the mitral annulus, and wherein the ring body defines a modified D-shape in atrial plan view with the anterior segment defining a relatively straight side as compared with the posterior portion that includes an outward curve, and with a minor axis extending between and bisecting the anterior segment and posterior portion and a major axis extending perpendicularly thereto, the major and minor axes being generally perpendicular to the flow axis, and wherein the posterior portion of the ring body has an outward bulge centered in the posterior portion that is radially outwardly curved more pronounced than adjacent sections of the posterior portion and creates a minor axis to major axis dimension ratio of between 3.44:4 (86%) and 3.6:4 (90%), wherein the ring body further includes an upward bow in the posterior portion.

15. The mitral annuloplasty ring of claim 14, wherein the axial height h of the upward bow is between about 3-10 mm.

16. The mitral annuloplasty ring of claim 14, wherein the outward bulge has an angular extent of between 80-90°.

17. The mitral annuloplasty ring of claim 14, wherein the upward bow has an angular extent approximately equal to the outward bulge.

18. The mitral annuloplasty ring of claim 14, wherein the upward bow has an angular extent greater than that of the outward bulge.

19. The mitral annuloplasty ring of claim 14, wherein the ring body defines a continuous, closed periphery.

20. The mitral annuloplasty ring of claim 14, wherein the ring body is saddle-shaped such that the anterior segment also defines an upward bow from adjacent sections.

* * * * *